US011219403B2

(12) United States Patent
Milner et al.

(10) Patent No.: US 11,219,403 B2
(45) Date of Patent: Jan. 11, 2022

(54) NEUROLOGICAL ASSESSMENT SYSTEM AND METHOD

(71) Applicant: BrainFx Inc., Markham (CA)

(72) Inventors: Tracy Milner, Uxbridge (CA); April Heather Condello, Whitby (CA)

(73) Assignee: BrainFx Inc., Pickering (CA)

( * ) Notice: Subject to any disclaimer, the term of this patent is extended or adjusted under 35 U.S.C. 154(b) by 157 days.

(21) Appl. No.: 14/771,735

(22) PCT Filed: Feb. 28, 2014

(86) PCT No.: PCT/CA2014/050153
§ 371 (c)(1),
(2) Date: Aug. 31, 2015

(87) PCT Pub. No.: WO2014/131131
PCT Pub. Date: Sep. 4, 2014

(65) Prior Publication Data
US 2016/0007905 A1    Jan. 14, 2016

Related U.S. Application Data

(60) Provisional application No. 61/771,443, filed on Mar. 1, 2013.

(51) Int. Cl.
*G16H 50/30* (2018.01)
*G16H 50/20* (2018.01)
(Continued)

(52) U.S. Cl.
CPC ............ *A61B 5/4088* (2013.01); *A61B 5/162* (2013.01); *A61B 5/165* (2013.01); *A61B 5/168* (2013.01);
(Continued)

(58) Field of Classification Search
None
See application file for complete search history.

(56) References Cited

U.S. PATENT DOCUMENTS 6,454,706 B1    9/2002  Pullman
6,820,037 B2 *  11/2004 Simon ................ A61B 5/16
                                              702/182
(Continued)

FOREIGN PATENT DOCUMENTS

CA    2680879 A1    9/2002
CA    2697566 A1    9/2010
(Continued)

OTHER PUBLICATIONS

NordCurrent; "101-in-1 Games (iPhone/iPod touch)"; Jan. 2010; https://www.youtube.com/watch?v=QSInudIXXJ8 (Year: 2010).*
(Continued)

*Primary Examiner* — William D Ermlick
(74) *Attorney, Agent, or Firm* — Schwegman Lundberg & Woessner, P.A.

(57) ABSTRACT

This document discusses, among other things, systems and methods configured to receive affect information from a patient in response to a provided affect inquiry and to receive real world activity information from the patient in response to a provided real world activity, and to provide patient neurofunction assessment information using the affect information and the real world activity information.

25 Claims, 4 Drawing Sheets

(51) Int. Cl.
  *A61B 5/00*  (2006.01)
  *A61B 5/16*  (2006.01)
(52) U.S. Cl.
  CPC .......... *A61B 5/4815* (2013.01); *A61B 5/4824*
    (2013.01); *A61B 5/7445* (2013.01); *A61B*
    *5/7475* (2013.01); *G16H 50/20* (2018.01);
    *G16H 50/30* (2018.01)

(56) References Cited

U.S. PATENT DOCUMENTS

| | | | |
|---|---|---|---|
| 6,896,656 B2 | 5/2005 | Krass | |
| 7,087,015 B1 | 8/2006 | Comrie et al. | |
| 7,294,107 B2 | 11/2007 | Simon et al. | |
| 7,837,472 B1* | 11/2010 | Elsmore | G06F 19/3487 434/236 |
| 7,890,340 B2 | 2/2011 | Abraham-Fuchs et al. | |
| 9,883,831 B1* | 2/2018 | Stewart | A61B 5/162 |
| 9,990,110 B1* | 6/2018 | Lounibos | G06F 3/04845 |
| 2003/0167149 A1* | 9/2003 | Simon | A61B 5/16 702/182 |
| 2005/0053904 A1* | 3/2005 | Shephard | G09B 7/00 434/236 |
| 2005/0187436 A1* | 8/2005 | Doniger | A61B 5/16 600/300 |
| 2006/0029912 A1* | 2/2006 | Kearby | G09B 21/009 434/116 |
| 2007/0282912 A1* | 12/2007 | Reiner | A61B 5/411 |
| 2008/0255949 A1* | 10/2008 | Genco | A61B 5/0205 705/14.4 |
| 2009/0043170 A1* | 2/2009 | Sulkin | A61B 5/1038 600/300 |
| 2009/0192417 A1 | 7/2009 | Mon-williams et al. | |
| 2009/0313047 A1* | 12/2009 | Smith | G06F 19/363 705/3 |
| 2010/0240016 A1* | 9/2010 | Ween | G06F 19/3481 434/236 |
| 2011/0065077 A1* | 3/2011 | Duffy | A61B 5/165 434/236 |
| 2011/0282682 A1* | 11/2011 | Whent | G06F 19/30 705/2 |
| 2012/0101346 A1 | 4/2012 | Scott | |
| 2012/0108909 A1 | 5/2012 | Slobounov et al. | |
| 2012/0202186 A1* | 8/2012 | Flood | G06Q 10/101 434/362 |
| 2012/0214143 A1* | 8/2012 | Severson | G06F 19/3431 434/236 |
| 2012/0221251 A1* | 8/2012 | Rosenberg | G06F 19/363 702/19 |
| 2012/0238831 A1* | 9/2012 | Benford | A61B 5/165 600/300 |
| 2013/0196295 A1* | 8/2013 | Post | A61B 5/16 434/219 |
| 2013/0209977 A1* | 8/2013 | Lathan | G09B 19/00 434/236 |
| 2013/0281794 A1* | 10/2013 | Murray | A61B 5/00 600/300 |
| 2013/0345593 A1* | 12/2013 | Burns | G06F 19/3431 600/558 |
| 2014/0047527 A1* | 2/2014 | Ngo | H04L 63/08 726/7 |
| 2014/0066802 A1* | 3/2014 | Kaula | A61B 5/16 600/554 |
| 2014/0295931 A1* | 10/2014 | Ng | A63F 13/2145 463/14 |
| 2014/0316220 A1* | 10/2014 | Sheldon | A61B 5/0205 600/301 |
| 2015/0017618 A1* | 1/2015 | Portenga | G09B 19/0038 434/236 |
| 2015/0038803 A1* | 2/2015 | Uhlig | A61B 5/4064 600/301 |
| 2015/0254994 A1* | 9/2015 | Smith | G09B 7/06 434/236 |
| 2015/0325132 A1* | 11/2015 | Sada | G09B 7/00 434/169 |
| 2016/0100788 A1* | 4/2016 | Sano | A61B 5/121 600/595 |
| 2017/0053540 A1* | 2/2017 | Meagher | G09B 5/00 |
| 2020/0222756 A1* | 7/2020 | Sano | A61B 5/4088 |

FOREIGN PATENT DOCUMENTS

| | | |
|---|---|---|
| WO | WO-87/07969 A2 | 12/1987 |
| WO | WO-2013149330 A1 | 10/2013 |
| WO | WO-2014131131 A1 | 9/2014 |

OTHER PUBLICATIONS

Morten Hertzum; "Perceived Time as a Measure of Mental Workload: Effects of Time Constraints and Task Success"; Apr. 2012; https://www.tandfonline.com/doi/abs/10.1080/10447318.2012.676538 (Year: 2012).*
"Application Serial No. PCT/CA2014/050153, International Preliminary Report on Patentability dated Sep. 11, 2015", 6 pgs.
"European Application Serial No. 14756509.7, Extended European Search Report dated Oct. 28, 2016", 8 pgs.
"European Application Serial No. 14756509.7, Office Action dated Oct. 23, 2015", 2 pgs.
"European Application Serial No. 14756509.7, Response filed Apr. 26, 2016 to Office Action dated Oct. 23, 2015", 22 pgs.
Kane, Robert L., et al., "Computerized Assessment in Neuropsychology: A Review of Tests and Test Batteries", *Neuropsychology Review*, 3(1), (1992), 1-117.
"BrainFx Prior Art Assessment", 8 pgs.
"International Application Serial No. PCT/CA2014/050153, International Search Report dated May 12, 2014", 3 pgs.
"International Application Serial No. PCT/CA2014/050153, Written Opinion dated May 12, 2014", 4 pgs.
"Canadian Application Serial No. 2,941,730, Office Action dated Jul. 12, 2017", 5 pgs.
"Canadian Application Serial No. 2,941,730, Response filed Jan. 12, 2018 to Office Action dated Jul. 12, 2017", 36 pgs.
"European Application Serial No. 14756509.7, Response filed May 12, 2017 to Extended European Search Report dated Oct. 28, 2016", 15 pgs.

* cited by examiner

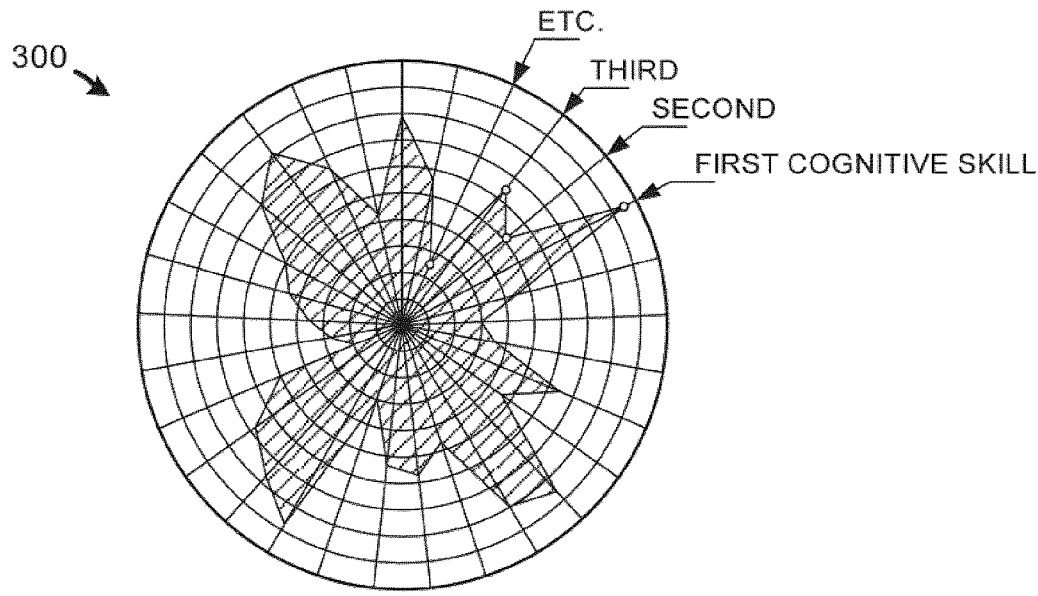

FIG. 3

| FOUNDATIONAL SKILLS | | INTERMEDIATE SKILLS | | COMPLEX SKILLS | |
|---|---|---|---|---|---|
| STRENGTH | CHALLENGE | STRENGTH | CHALLENGE | STRENGTH | CHALLENGE |
| MEMORY – IMMEDIATE – FOR VISUAL SPATIAL | MEMORY – IMMEDIATE – FOR AUDITORY | PROBLEM SOLVING | MEMORY – DELAYED – FOR WRITTEN AND CUED | JUDGEMENT<br><br>COMPRE-HENSION OF HUMOR AND INFERENCES | ATTENTION – DIVIDED<br><br>FORESIGHT |
| COMPOSITE SCORE: | | COMPOSITE SCORE: | | COMPOSITE SCORE: | |
| COMPARISON TO SIMILAR HEALTHY/SELECTED IMPARIED POPULATION: STRENGTH/CHALLENGE | | COMPARISON TO SIMILAR HEALTHY/SELECTED IMPARIED POPULATION: STRENGTH/CHALLENGE | | COMPARISON TO SIMILAR HEALTHY/SELECTED IMPARIED POPULATION: STRENGTH/CHALLENGE | |

FIG. 4

NEUROLOGICAL ASSESSMENT SYSTEM AND METHOD

CLAIM OF PRIORITY

This application is filed in the U.S. as a National Stage Filing under 35 U.S.C. 371 of PCT application PCT/CA2014/050153, filed Feb. 28, 2014, which claims the benefit of priority under 35 U.S.C. § 119(e) of U.S. Provisional Patent Application Ser. No. 61/771,443, titled "NEUROLOGICAL ASSESSMENT SYSTEM," filed on Mar. 1, 2013, which are incorporated by reference herein in their entirety.

BACKGROUND

It is estimated that one in three people will suffer some sort of brain disorder over their lifetime. A majority of brain disorders are mild, and even remain undiagnosed. However, brain disorders are still responsible for more death and disability than both cancer and cardiovascular disease combined.

Cognition is the mental process of knowing, and includes aspects such as awareness, perception, reasoning, and judgment. Various cognitive assessment tools have been used to assess cognitive function in patients with severe brain disorders to diagnose the type of injury, the area of injury, or to monitor patient progress. However, existing cognitive assessment tools fail to assess cognitive function of patients with mild to moderate impairments.

OVERVIEW

This document discusses, among other things, systems and methods configured to receive affect information from a patient in response to a provided affect inquiry and to receive real world activity information from the patient in response to a provided real world activity, and to provide patient neurofunction assessment information using the affect information and the real world activity information.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 illustrates generally example patient neurofunction assessment information.

FIG. 4 illustrates generally example neurofunction assessment information including patient strengths and challenges in real world function.

DETAILED DESCRIPTION

Brain disorders vary from concussions and traumatic brain injuries (TBI) to dementia, neurodegeneration, stroke, and mental illness, each type ranging in severity, from mild to moderate or severe. Many existing cognitive assessment tools focus on diagnosing severe impairment, but struggle with mild to moderate brain disorders. In contrast, the systems and methods disclosed herein are configured to identify strengths and challenges in patient neurofunction using real world activity information, in certain examples, especially applicable to patients with mild to moderate brain disorders.

The present inventors have recognized, among other things, computerized assessment systems and methods to comprehensively assess neurofunction of a patient using a neurological assessment tool, such as a web-enabled, portable, touch-screen tablet computer, smartphone, or one or more other computing devices configured to receive information from a patient or one or more other third parties separate from the patient using one or more input on the neurological assessment tool. Neurofunction can refer to, for example, a functional status of a patient as related to their neurological condition, whether healthy or dysfunctional, including their abilities (physical, cognitive, psychosocial), activity participation, or quality of life.

Figure 1:
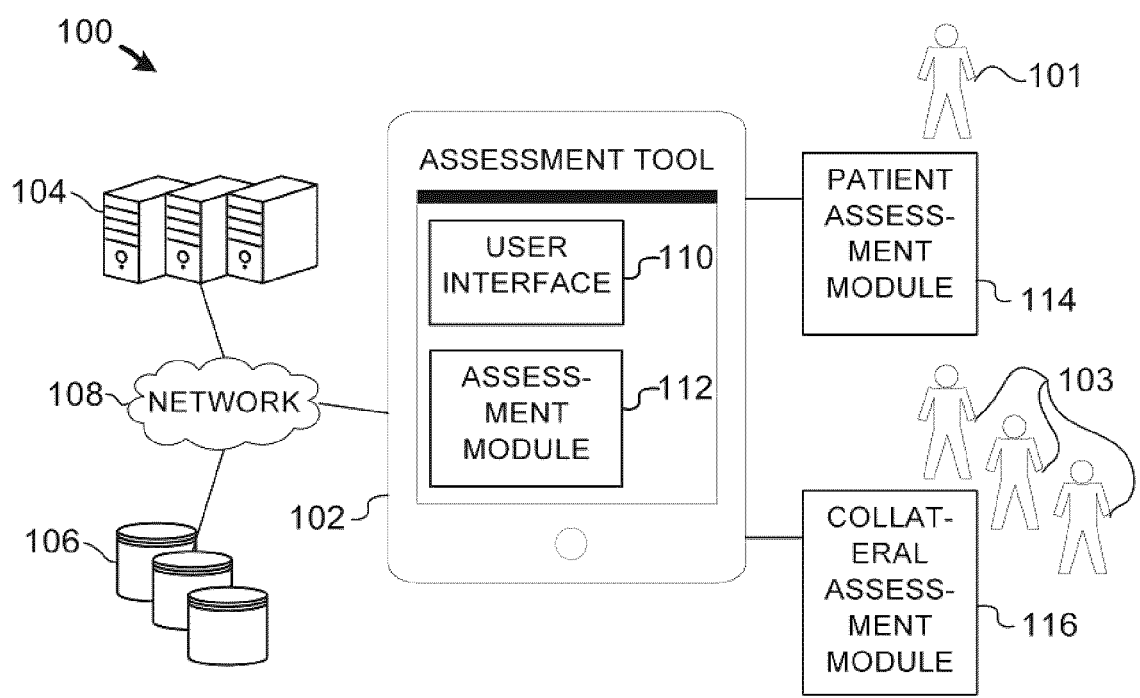
FIG. 1 illustrates generally an example computerized assessment system including a neurological assessment tool and an assessment module.

FIG. 1 illustrates generally an example computerized assessment system 100 including a neurological assessment tool 102 including a user interface 110 and an assessment module 112 configured to provide patient neurofunction assessment information. In an example, the neurological assessment tool 102 can include a tablet computer, a smartphone, or one or more other computing devices including a patient assessment module 114 configured to receive affect information from a patient 101 in response to a provided affect inquiry, and to receive real world activity information from the patient 101 in response to a provided real world activity. In an example, the user interface 110 can include one of a plurality of interfaces configured to provide communication between the neurological assessment tool 102 and the patient 101, a clinician or other caregiver, or one or more other users. The user interface 110 can include, but is not limited to a display, a touch screen input, a keyboard, a mouse, a camera, a microphone, a gyroscope, an accelerometer, or one or more other inputs. In certain examples, the neurological assessment tool 102 can be configured to receive information (e.g., affect information, real world information, etc.) from the patient 101 through selection, touch (e.g., draw, slide, tap, pinch, etc.), auditory, verbal, and accelerometer/gyroscope, or one or more other techniques.

In an example, the neurological assessment tool 102 can be configured to provide at least one of the affect inquiry or the real world activity to the patient 101. In other examples, one or more other devices can be configured to provide the affect inquiry or the real world activity to the patient 101, or at least one of the affect inquiry or real world activity can be delivered through a clinician or other caregiver.

The assessment module 112 can be configured to provide patient neurofunction assessment information, such as strengths and challenges in real world functions, using the received affect information and real world activity information from the patient 101. In an example, the assessment module 112 can be configured to output the patient neurofunction assessment information to the patient 101, a clinician or caregiver, or one or more other users. In an example, the assessment module 112 can be located remote from the neurological assessment tool 102, such as in a server 104 coupled to the neurological assessment tool 102 over a network 108. Patient data can be stored in the neurological assessment tool 102, the server 104, or in a database 106 remote from the server 104 and the neurological assessment tool 102.

In an example, the neurological assessment tool 102 can include a collateral assessment module 116 configured to receive collateral input from a third party 103 separate from but close to the patient 101 in response to a collateral inquiry. In an example, the neurological assessment tool 102 can be configured to provide the collateral inquiry to the third party 103. In certain examples, the third party 103 can include a plurality of separate collateral inputs, such as from a group of individuals familiar with the patient 101.

In an example, an assessment module 112 can be configured to provide patient neurofunction assessment information using affect information and real world activity information received from a patient 101, and collateral input received from one or more third party 116 separate from the patient 101. In certain examples, the computerized assessment system 100 can be configured to supplement information received from the patient with one or more collateral inquiries.

The present inventors have recognized that various affect inquiries can be provided to improve ecological validity of a cognitive assessment. In an example, the computerized assessment system 100 can be configured to provide a questionnaire to a patient followed by various affect inquires. Both the questionnaire and the affect inquiries can be configured to determine patient status with respect to various statistical mitigators, examples of which are illustrated in Table 2. However, affect inquiries focus on the current condition of a patient while undergoing assessment, whereas the questionnaire focuses on background information and statistical mitigators leading up to the assessment (e.g., the prior week, etc.). In certain examples, affect information received from the patient 101 can alter the remainder of the cognitive assessment (e.g., the real world activities, scoring of responses, etc.).

Further, the cognitive assessment can be composed of various real world activities, such as event planning, comprehension of humor, or recognition of dangerous conditions, and that the output of the assessment module 112, instead of identifying a severity or type of injury, can identify strengths and challenges in patient neurofunction with respect to real world functions, such as illustrated in FIGS. 3 and 4.

The computerized assessment system 100 can provide an output, such as a report, including, for example, a self report using information from the patient 101, a collateral report using information from the third party 103 separate from the patient 101, or performance data from the computerized assessment. Results can be compared, for example, using statistical relevance, to a healthy or known population or to a previous baseline established by the patient 101 to demonstrate whether the performance is impaired. If a previous assessment has been completed, the assessment module can compare results to one or more previous performances and statistical relevance can be determined.

Example Questionnaire

In an example, the computerized assessment system 100 can be configured to provide a questionnaire to the patient, including, for example, at least one of biographical information, medical history, sleep information, nutrition information, symptoms, daily activities, quality of life, level of experience with technology, reasons for completing the assessment, etc. The computerized assessment system can be configured to receive information from the patient in response to the provided questionnaire. In certain examples, the affect inquiries and real world activities provided to the patient can depend at least in part on the information received from the patient in response to the questionnaire. For example, if a patient is familiar with the technology, more complex real world activities can be presented to the patient for use in the assessment. In contrast, if a patient is not familiar with tablet computer inputs (e.g., multi-touch input, etc.), the real world activities presented to the patient can be tailored to the patient experience level, or the resulting assessment can be weighted accordingly.

In certain examples, the patient can invite a third party (e.g., more than one, up to three, etc.), separate from the patient, to provide collateral information about the patient. The computerized assessment system can be configured to receive information from the third party about the patient, including, for example, at least one of patient sleep information, patient nutrition information, patient symptoms, daily activity of the patient, patient quality of life, or other patient information.

Provided questions or inquiries can have different response options, such as numeric, binary, or other. Other responses, such as qualitative responses, can be stored in text form. In an example, when information is received from the patient, the assessment module can be configured to store the following information illustrated in Table 1.

TABLE 1

| Own Healthy Baseline (if available) | Healthy Population | Follow-Up Assessment | Collateral Report | Degree of Change |
| --- | --- | --- | --- | --- |
| Actual Response | Mode with percent of population | Actual Response | Actual Response | If yes/no, a change in response is color coded. If two to five options, a change in one unit is color coded yellow, while a change of more than two units is color coded red. Percent change is used where numerical. |

In Table 1, a baseline is a previous assessment. In certain examples, the baseline assessment is the prior assessment. In other examples, one or more other assessments have occurred between the baseline assessment and the current or next assessment. A healthy population is a composed of assessments from multiple healthy individuals. A follow-up assessment is the current assessment to be compared to the baseline assessment. If there is an existing baseline to which the current assessment can be compared then each score is compared to the selected baseline assessment and is displayed with the percent change.

A collateral report is information about the patient from a third party separate from but familiar with the patient. The degree of change signifies the amount of difference between the baseline assessment and the follow-up assessment, where the Percent Change=Baseline−Follow up/Baseline.

Standardized Performance Assessment

In certain examples, after receiving questionnaire information from the patient, the neurological assessment tool can be configured to provide standardized performance assessment activities or inquiries to the patient. Table 2, below, illustrates approximately 50 real world example activities that can be provided to the patient, using, for example, a computerized assessment system. In an example, the computerized assessment system can include a tablet or other portable or stationary computer having one or more inputs configured to receive information from the patient to assess cognition, mood, pain, anxiety, sensory skills, fine motor skills, balance, etc. In certain examples, one or more of the real world activities can be delivered as functional, game-like, everyday activities, such as identifying safety hazards in images, etc.

In an example, the computerized assessment system can include a database configured to store a large number of different real world activities. When a patient undergoes multiple assessments close in time, different real world activities can be provided (e.g., randomly) to minimize the probability of learning effecting performance, which has been a criticism of other clinical assessment tools and have affected their clinical utility, requiring six months to a year between assessments. For example, in the activity where four words need to be remembered, these 4 words are randomly chosen from a database of words (e.g., greater than 20 words, etc.). In other examples, (e.g., the fundraising activity shown in Table 2, below), the concept can remain the same, but another version can be drawn from the bank of versions where details of the tasks and rules are changed. In certain examples, each activity can be time limited, with a maximum amount of time assigned to each activity.

In an example, the computerized assessment system can be configured to provide one or more of the following activities illustrated in Table 2, including a description of each activity, how the neurological assessment tool is configured to interact with the patient, how the data is sorted, and the skill the activity is mapped to.

TABLE 2

| Num | Activity | Description | How Data Collected | Data Scoring | Maps to Skill |
|---|---|---|---|---|---|
| 1 | Fatigue | How tired are you feeling now? Not at all, a little, somewhat, very, extremely | Touch to select | Display (Statistical Mitigator) | Affect at time of assessment |
| 2 | Sleep | # hours of sleep last night (5 options: less than 5, 5-7, 7-8, 8-9, more than 10) | Touch to select | Display (Statistical Mitigator) | Affect at time of assessment |
| 3 | Mood | How are you feeling on the Mood Scale? [in words] Visual analog scale from 0 to 10; sad to happy | Touch to select | Display (Statistical mitigator) | Affect at time of assessment |
| 4 | Pain | Are you experiencing pain? [in words] Visual analog scale from 0 to 5; pain free to painful | Touch to select | Display (statistical mitigator) | Affect at time of assessment |
| 5 | Font Size | Which size do you find most comfortable to read? Sentences presented to read aloud from larger to smaller | Touch to select | Display font size able to read (pre-requisite) | Sensory - visual acuity |
| 6 | Read Passages Aloud | Read a paragraph aloud and administrator chooses quality of how read from four options | Verbal Touch to select | Display result (pre-requisite) | Reading |
| 7 | Hand Dominance | Which hand do you write with? Right, Left, Both | Touch to select | Display (Background) | Background |
| 8 | Touch objects as they appear | 15 pictures appear at varying speeds that need to be touched | Touch to select (Multiple) | Pre-requisite - must be able to complete or unable to continue Display time ** | Sensory - neglect in midline |

TABLE 2-continued

| Num | Activity | Description | How Data Collected | Data Scoring | Maps to Skill |
|---|---|---|---|---|---|
| 9 | Color Blindness | 3 plates discerning if they can read to number within the plate presented | On-screen touch number pad w Enter | # correct/3 Pre-requisite - must be able to complete or unable to continue | Sensory - color blindness |
| 10A | Anxiety | How anxious are you feeling right now? Multiple choice - Extremely, Somewhat, A Little, Not at all | Touch to select | Display (Statistical Mitigator) | Affect early in the assessment |
| 10B | Anxiety (repeated) | 23 activities later - they are asked again about level of anxiety as per above | Touch to select | Display (Statistical Mitigator) | Affect later in the assessment |
| 11 | Headphone check | Can you hear the crowd cheering? Yes/No | Touch to select | Pre-requisite - must be able to complete or unable to continue | N/a |
| 12A | Hearing Test | 20 sounds from 15 Hz to 21000 Hz are presented and client presses 'heard sound' when they can hear sound | Touch to select | Pre-requisite - must be able to hear middle range sounds or unable to continue Display the Hz of the sounds heard Determine range of sounds client able to hear Identify if there are inconsistencies in range (e.g., missed sounds within range that they were able to hear) | Sensory - hearing |
| 12B | Hearing Test - by Side | 9 sounds split between left, right, and both ears. Listen to sound and person presses whether heard in left, right or both ears. | Touch to select | #correct/9 Determine if any pattern - e.g., can't hear on left or right and to which range - high, medium, low | Sensory - hearing |
| 13A | Shape cut out | A shape is cut out of a solid rectangle and need to select which of 4 shapes were cut out - 2 rounds | Touch to select | #correct/2 | Visual perception - spatial |
| 13B | Visual closure | A solid drawing is shown and need to choose which of the four dotted drawings match it 2 rounds | Touch to select | #correct/2 | Visual perception - closure |
| 13C | Match and scan numbers | A two-digit number is highlighted to match on screen with same numbers in different order with only five matches to be made 2 rounds | Touch to select (multiple) | #found/5 X 2 False positives: # ** Score: #found/10 minus false positives | Sensory - visual scanning |

TABLE 2-continued

| Num | Activity | Description | How Data Collected | Data Scoring | Maps to Skill |
|---|---|---|---|---|---|
| 13D | Word fit | A word is presented and need to select from four options which box it fits into 2 rounds | Touch to select | #correct/2 | Visual perception - spatial |
| 13E | Rotation | A drawing is presented and it needs to be drawn to specified rotation - ¼ or ½ turn 2 rounds | Draw | Display beside target response Determine if correct: CBA responds Yes (1 pt) or No (Opt) ** Display time | Visual perception - rotation |
| 13F | Mirror Images | A drawing is presented that needs to be completed via mirror image 2 rounds | Draw | Display beside target response Determine if correct: CBA responds Yes (1 pt) or No(Opt) ** Display time | Visual perception - mirror |
| 13G | Copy complex drawing | A drawing is presented that needs to be copied | Draw | Display beside target response Determine if correct: CBA responds: Completely accurate (2 pt) or Partially Accurate (1 pt) or Not Accurate (0 pt) ** Display time | Visual perception - Complex copy |
| 13H | Clock draw | Instruction provided to draw face of clock with time set to a specific time | Draw | Display beside target response By CBA: Planning Points: Clock face (1) Clock numbers shown (1) Clock numbers accurate (1) Long hand for minute (1) Short hand for hour (1) Total #/5 Spatial Points: Circle face, not oval/other shape (1) Numbers in proper positions (1) Right time displayed (1) ** Display time | Visual perception - spatial, planning |
| 14 | Find the Differences | Two pictures presented; picture on right has 6 differences that need to be found | Touch, to select (multiple) | #correct/6 ** Display time | Attention- Selective (to detail) |
| 15A | Items to remember | Coach asks person to remember four items (randomized | Type (multiple) | #words/4 #trials **Display time | Immediate memory - to auditory |

TABLE 2-continued

| Num | Activity | Description | How Data Collected | Data Scoring | Maps to Skill |
|---|---|---|---|---|---|
| | | from bank of variables) and they need to type them in; they can listen up to three times | | | |
| 15B | Items to remember | 15 questions later; asked to recall the items by typing in | Type (multiple) | #/4 ** Display time | Delayed memory - auditory and written |
| 16 | Part of Day | What part of the day is it? Morning, Afternoon, Evening | Touch to select | Display target response and actual response Determine if correct (Y/N)' | Temporal awareness |
| 17A | Math questions - no distraction | 20 math questions that include all four operations are presented and answers submitted via on screen key pad | Onscreen touch number pad w Enter | #correct/20 ** Display time | Simple to moderate problem solving |
| 17B | Math questions - with distraction | 18 activities later; more math equations are completed with audio distraction of crowd cheering | Onscreen touch number pad w Enter | #correct/20 ** Display time Difference in number correct and time between no distraction and distraction | Selective attention |
| 18A | Press logo when a particular sound played | Plays sound and instructs person to touch logo next time they hear it and type in the sentence that is displayed | — | — | — |
| 18B | Sound plays to cue to touch logo | Sound plays 12 activities later to cue person to touch logo then type the sentence they were to recall | Touch to select Type sentence | Recalled Y/N Sentence typed Y/N Display target sentence and written sentence | Prospective memory to auditory cue, 2 step |
| 19 | Puzzle | An easier and more complex puzzle are displayed then broken into 9 pieces to be rebuilt 2 rounds | Slide (multiple pieces) | Completed correctly? Y/N For each one. #of pieces correctly placed for Puzzle 1 Puzzle 2 (more challenging) | Constructive ability |
| 20A | Remember this person's picture | A photo of a person is shown and they are to touch the picture next time that they see it in the assessment | — | — | — |
| 20B | Touch person's picture | 13 activities later, the picture of the person is in another activity, they need to touch it if they recognize it | Touch to select | Recalled? Y/N | Prospective memory to visual cue |
| 21 | Making change | Need to enter how much change is expected given money given and cost of purchase 2 rounds | Onscreen touch number pad with Enter | #correct/2 ** Display time for each | Simple problem solving |

TABLE 2-continued

| Num | Activity | Description | How Data Collected | Data Scoring | Maps to Skill |
|---|---|---|---|---|---|
| 22A | End of Test Gesture | Shown the screen at the end of the assessment and asked to remember to vertically swipe it at the end of the assessment when shown for reward | — | | — |
| 22B | End of Test screen | 25 activities later need to recall to vertically swipe the picture and then music will play | Vertical swiping over image | Recalled Y/N | Prospective memory to visual cue |
| 23 | Route finding on map | A map of a town with familiar types of locations displayed; asked to find most direct route between two locations - a simple one and a harder one; then asked to route between, two locations making two stops along the way | Tracing a route leaving breadcrumbs | Destination reached? Y/N (round 1, round 2) Efficient route Y/N Each round total of 2 Additionally for complex were the en route destinations reached? Efficient Y/N Total of 4 for complex | Route Finding |
| 24 | Candy Jar | Asked to slide and pinch candies into the jar as quickly as possible (visual highlight when in target zone) Practice round 5 candies with left 5 candies with right 10 candies alternating 9 between left and right 10 candies pinching (sound feedback with pinch) | Sliding to jar lid Pinching to jar lid | ** Left - time Right - time Alternating - time Pinching - time | Fine motor speed and coordination |
| 25A | Meet your team | Presented with a large group of people and need to remember the faces (20) and names (5 of 20) while party conversation plays in headphones | Touch to select; Touch to close | #/20 met | Temporal awareness |
| 25B | Recall your team | 12 activities later they are shown 30 pictures (20 team members, 10 visitors) and asked to slide each person to either Home Team (Your Team) or Visitors' Team (Other Team) | Slide to location (multiple options) Type in names | #correctly identified from previous #false positives #names/5 correctly remembered | Delayed recall - to faces and names |

TABLE 2-continued

| Num | Activity | Description | How Data Collected | Data Scoring | Maps to Skill |
|---|---|---|---|---|---|
| | | and if they know their name to type it | | | |
| 26A | Thinking of items in category | A category is presented; need to type in as many items as possible during time that belong the category 2 rounds | Typing | Display items #items correct to category | Mental flexibility |
| 26B | Thinking of items in category with distraction | 9 activities later as above but with crowd cheering at same time 1 round | Typing | Display items #items correct to category Difference in # of items | Selective Attention |
| 27A | Thinking of category from items | Up to six items are presented and the category is typed in as soon as known | Typing | Correct category? Y/N Display items entered #entries to correct answer Time to correct response | Abstract reasoning |
| 27B | Thinking of category from items with distraction | 8 activities later as above but with crowd cheering at same time | Typing | Correct category? Y/N Display items entered #entries to correct answer Time to correct response Compare #entries and time to correct with no distraction | Selective Attention |
| 28A | Sticky Note with Appt Details | A sticky note is displayed with four details about an appointment that need to be recalled for later (who, time, date, place) | — | — | — |
| 28B | Recall appointment details | 7 activities later asked to recall details of appointment and type them into four provided spaces cued by who, date, time and place. | Typing | Display responses beside target response #details/4 correct | Delayed memory - to written with cues |
| 29A | Put pictures in order | 5 pictures of household task are presented and need to slide them into order | Sliding to location | #/5 in correct location ** Time to complete | Sequencing ~ to pictures |
| 29B | Putsentences in order | 8 sentences are displayed and need to slide them into the correct order (familiar and less familiar functional activities) 3 rounds | Sliding to location | #/8 in correct location ** Time to complete | Sequencing - written steps |
| 30 | Recall player positions (5 Sets) with and without audio background | Players dressed in red and blue jerseys are presented on screen - asked to remember location of players in red | Touch to select (multiple) | #/3, 4, or 5 recalled Compare to distraction to no distraction | Immediate memory - visual spatial |

TABLE 2-continued

| Num | Activity | Description | How Data Collected | Data Scoring | Maps to Skill |
|---|---|---|---|---|---|
| | | jerseys (randomized location) with 3, 4 and 5 players in red. Two rounds with audio playing of crowd cheering. 5 rounds | | | |
| 31 | Touch Emotions | 4 pictures of people with different emotions and asked to select the picture of emotion requested 4 rounds | Touch to select | #/4 correct | Social skill - recognizing emotion |
| 32 | Sorting into categories (20 Items to Sort) | 20 household items (randomized from bank of items) are presented and need to slide them to the category where they best fit: school bag, drawers, kitchen cupboards, fridge/freezer, or sports bag | Slide to location (multiple choices) | #/20 into correct category ** display time | Abstract reasoning - Categorizing |
| 33 | Time since started Ax (recall picture here also) | How many minutes have passed since you started the assessment? Enters number of minutes | Onscreen touch key pad with Enter | Display time started and time estimated Display difference | Temporal Awareness |
| 34 | Bigger picture (2 rounds) | An illustration (randomized from bank of illustrations) is shown and asked 'What is going on or what has happened in this picture' and person responds out load to time limit and then administrator checks off which key messages were heard and whether right away or later in response 2 rounds | Touch to select (multiple) | For each round - display #/key messages; display whether immediate or eventual | Abstract reasoning - Big picture thinking |
| 35 | Fundraiser planning | In a paragraph there is a description of 11 tasks that need to be completed over the course of the day to assist with a fundraiser. They have rules and nuances to them that indicate that they need to be organized into a particular order for efficiency. By touching or | Touch, hold and slide; Slide to move; Touch to select | #/11 tasks placed on agenda #/XX rules followed in ordering tasks ** Display time out of available time | Executive Functioning - planning, organizing, implementing, reviewing/reflecting |

TABLE 2-continued

| Num | Activity | Description | How Data Collected | Data Scoring | Maps to Skill |
|---|---|---|---|---|---|
| | | holding and sliding them the tasks are put on the agenda for the day by time. | | | |
| 36 | Identifying safety hazards | 10 pictures (randomized from bank of pictures) are presented and need to identify all the hazardous pictures 2 rounds | Touch to select (multiple) | #/12 safety hazards identified | Judgment for safety - Identification |
| 37 | Unsafe consequences | A picture is shown of a safety hazard and they are asked what is the worst that could happen and select: Death or severe injury, minor injury, Inconvenience or additional work, Nothing. 4 rounds | Touch to select | #/4 correct Display target and actual response for each | Foresight for safety |
| 38 | What to do re: safety | Then they are asked if the worst does happen, what needs to be done: call emergency services, seek medical treatment on your own, call service professional or fix yourself, or Nothing 4 rounds | Touch to select | #/4 correct Display target and actual response for each | Judgment for safety - Action |
| 39 | Modified Stroop Test | Asked to ignore the what the word reads but touch the color that the word is written in (which is different) 15 Rounds | Touch to select | #/15 correct ** display time | Impulsivity |
| 40A | Online Banking (>18 years old) | Instructions on a home screen to pay three bills (set date for them) and to transfer money from checking to savings account on pay day, but no overdraft and can't move money from savings | Touch to select Onscreen numeric key pad for amount | All bills paid = 1 No negative, balance = 1 Money transferred correctly = 1 Score out of 3 ** Display time | Executive functioning & Combined Skills |
| 40B | Homework planning (<18 years old) | Instructions home screen to study for a quiz, complete an assignment and study for a test on different dates, with rules related to other time commitments over the course of a week. Press To-Do List button to get to list of tasks, | Touch to select Slide to move | All school tasks scheduled = 1 No conflicts = 1 # Rules following = up to 3 | Executive functioning & Combined Skills |

TABLE 2-continued

| Num | Activity | Description | How Data Collected | Data Scoring | Maps to Skill |
|---|---|---|---|---|---|
| | | description and their due date. Slide tasks into weekdays displayed at bottom of screen | | | |
| 41 | Matching - don't let the pot boil over | Need to match as many objects as possible in the kitchen scene while watching that the pot on the stove does not boil over and moving it to remove water from it before it does | Touch to select matches Touch and slide to sink | # Matches made #pots moved/ # pots Score weights each task equally | Divided attention |
| 42 | Listen to a Lecture | A lecture of approximately 1 minute 15 seconds is listened to on a novel topic. After the person says everything that they can remember and the administrator checks off which of the 20 details they recalled. | Touch to select (multiple) | #details/20 recalled | Immediate memory - to auditory, complex, novel |
| 43 | Prioritizing tasks | Tasks are presented with differing levels of priority and need to be slid into order of priority - highest priority on top 4 rounds - 2 with 3 tasks; 2 with 5 tasks | Slide to move | #/3 or 5 in correct position ** display time | Prioritizing |
| 44 | Driving | Hand Controls for everything. Press and Hold for the Gas and brake. Gas off, decrease speed at 50% rate of accelerating. Turn Signal is the actuator to make the turn when the auto arrives at the corner. Scene set so there is enough distance between intersections so that a turn is always the "next intersection". It is First person perspective, inside the car, Windshield frame, left hand, right hand, windshield mirrors. Mirrors are grey until a single object appears. Suburban scene, houses, trees, | Touch for gas, brake, turn. Accelerometer for speed. | Appropriate speed = 1 pt for each turn completed at appropriate speed Avoids obstacles = # of obstacles avoided/ number presented Re-routed safely = # times/# presented ** Time to complete course | Executive functioning & Combined Skills |

TABLE 2-continued

| Num | Activity | Description | How Data Collected | Data Scoring | Maps to Skill |
|---|---|---|---|---|---|
| | | road, cars, pedestrians, cyclists, stop signs, left hand turn lanes. GPS is a Map navigation Window view on the current section. Audio sounds played for contact with objects. Cyclist in the right mirror remains visible during the turn, then is down on the road. Practice session at start that has them go thru 2 stop signs. Total test time 5 minutes. Driving tasks - straight, right turn, left turn, avoid obstacles/detour, busy left hand turn with obstacles; don't pay attention to distractors. Time to complete. | | | |
| 45 | How many people on the train? | The number of people on a train are shown before the train drops over them and people move onto the train and people move off the train. Need to keep count of how many people are on the train. 2 rounds - slower, faster | Onscreen numeric keypad with Enter | #/2 correct | Working memory |
| 46 | Conversation at party | Person listens to a conversation between two people who haven't seen each other in a long time with background party noise and a secondary conversation nearby. They then answer 5 multiple choice questions about details or inferences from the conversation | Touch to select | #/5 correct Display target response and actual response ** Display time to complete the 5 questions | Selective Attention Comprehension of humor and inferences |
| 47 | Balance Testing | Tablet is positioned horizontal at hip level against the body Person is measured for 30 | Gyroscope reading | Display performance on graph Compare difference between eyes open and eyes | Static Balance |

TABLE 2-continued

| Num | Activity | Description | How Data Collected | Data Scoring | Maps to Skill |
|---|---|---|---|---|---|
| | | seconds in the following positions: Standing, both feet, eyes open Standing, both feet, eyes closed Tandem, eyes open Tandem, eyes closed Left foot, eyes open Right foot, eyes closed | | closed; left foot and right foot | |
| 48 | Time | Time is tracked by question where is there is an asterisk in the scoring section of the question above; as well as time of pauses; as well as overall time | — | Add up all the time of those selected above and display (A) Add up pauses and display (B) Add up total amount of time of assessment (C) A + B/C | Information processing speed |
| 49 | Administrator Notes: About information processing speed | Administrator rates their observation of and opinion on information processing speed: Much slower than Normal; Slightly slower than Normal; Normal | Touch to select | Display response | Information processing Speed |
| 50 | Administrator Notes: About Endurance | Administrator rates their observation of and opinion on endurance: Much less than normal Slightly less than normal Seemed about normal | Touch to select | Display response | Endurance |
| 51 | Administrator Notes: About Comprehension and Communication | Administrator rates their observation of and opinion on comprehension and communication: Much more difficult than normal Slightly more difficult than normal Seemed about normal | Touch to select | Display response | Comprehension and Communication |
| 52 | Administrator Notes: About Mood and Behavior | Administrator rates their observation of and opinion on information processing speed: Significant fluctuations in mood and behavior Slight fluctuations in mood and | Touch to select | Display response | Mood and Behavior |

TABLE 2-continued

| Num | Activity | Description | How Data Collected | Data Scoring | Maps to Skill |
|---|---|---|---|---|---|
| 53 | Administrator notes - Other | behavior Expected mood and behavior Administrator documents additional notes about the assessment: that may affect validity, informal observations, more details on the above areas | Type | Display text | Additional Notes |

Reporting by Area/Cognitive Skill

Each activity in Table 2 maps to a cognitive skill. The computerized assessment system can include an assessment module configured to provide neurofunction assessment information using the information received from the patient in response to each provided activity. In an example, the neurological assessment tool or one or more other display can be used to provide an assessment report. Details of the assessment report are important to different disciplines of healthcare professionals as they examine the data as related to their scope of practice, to assist with clinical diagnosis, treatment planning, or other recommendations.

The assessment module can be configured to break the measured skills into separate categories, each serving a separate purpose. For example, Table 3 illustrates patient affect inquiries at the time of assessment and associated affect measurement information, whereas Table 4 illustrates patient sensory and pre-requisite skills to perform such assessment.

TABLE 3

Affect at Time of Assessment:

| Area | Measurement |
|---|---|
| Fatigue | Comparison to own baseline if available |
| Sleep | Mode of normal population; % of population |
| Anxiety - early in assessment | If two to five options: |
| Anxiety - late in assessment | A change in one unit is color coded yellow. A change of more than 2 units is color coded red. |
| Mood | |
| Pain | Additionally for anxiety, early and late are compared to each other. |

TABLE 4

Sensory & Pre-Requisite Skills:

| Visual | Hearing | Reading |
|---|---|---|
| Acuity | Range Left/Right/Both ears | Ability to read paragraph aloud |
| Neglect | | |
| Color blindness | | |
| Visual perceptual skills - a total score is added; details are also provided by each type of visual perceptual skill: | | |
| Spatial (13A + 13D + 13H spatial points) | | |
| Scanning | | |

TABLE 4-continued

Sensory & Pre-Requisite Skills:

| Visual | Hearing | Reading |
|---|---|---|
| Rotation | | |
| Mirror | | |
| Copy | | |
| Planning (13H planning points) | | |

For each activity, assessment information, such as that displayed in Table 1, can be stored for the patient.

Many of the skills displayed in Table 2 are mapped to multiple activities. For example, the skill, "Attention-Selective-To Auditory Distraction," is mapped to activities 17B, 26B, 27B, and 46. In certain examples, a specific activity mapped to a specific skill can better indicate patient strength or challenge associated with that skill. Accordingly, different activities can have different weights when assessing neurological function with respect to said activity, as illustrated in Table 5.

TABLE 5

| Cognitive Skill | Activity # included and Weighting (if applicable) |
|---|---|
| Attention - Selective - To Visual Distraction | 14 |
| Attention - Selective - To Auditory Distraction | 17B -10% 26B - 25% 27B - 25% 46 - 40% |
| Attention - Divided | 41 |
| Memory - Immediate - For Auditory | 15A |
| Memory - Immediate - For Visual Spatial | 30 |
| Memory - Immediate - For Auditory, Complex, Novel | 42 |
| Memory - Delayed - For Auditory & Written | 15B |
| Memory - Delayed - For Face and Names | 25B |
| Memory - Delayed - For Written and Cued | 28B |
| Memory - Prospective - Auditory, 2 steps | 18B |
| Memory - Prospective - Visual Cue | 20B - 50% 22B - 50% |
| Memory - Working | 45 |
| Temporal Awareness | 16 - 20% 25A - 50% 33 - 30% |
| Problem Solving | 21 - 40% 17A 60% |

TABLE 5-continued

| Cognitive Skill | Activity # included and Weighting (if applicable) |
|---|---|
| Constructive Ability | 19 |
| Route Finding | 23 |
| Sequencing | 29A (20%) |
| | 29B (80%) |
| Emotion Recognition | 31 |
| Mental Flexibility | 26A |
| Abstract Reasoning | 27A - 30% |
| | 32 - 20% |
| | 34 - 50% |
| Judgment for safety | 36 - 40% |
| | 38 - 60% |
| Foresight for safety | 37 |
| Impulsivity | 39 |
| Comprehension & Humor Inferences | 46 |
| Executive Functioning and Combined Skills | 35 - 30% |
| | 40A or 40B (by age) - 20% |
| | 43 - 10% |
| | 44 - 40% |
| Information Processing Speed | 48- 80% |
| | 49- 20% |
| Endurance | 50 |
| Comprehension & Communication | 51 |
| Mood and Behavior | 52 |

TABLE 6

| Physical Skill | Activity # included and Weighting (if applicable) |
|---|---|
| Fine Motor | 24 |
| Balance | 47 - comparison in overlaying graphs |

The cognitive skills can be displayed on a web graph, such as illustrated in the example of FIG. 3. Further, for each of the above, assessment information, such as that displayed in Table 1, can be stored for the patient, such as in a database 106. Further, any background information on the patient collected during the assessment, such as medical history, medications, medication dosage, demographic information, diet, exercise habits, general sleep quality, etc., can be indexed and stored in the database 106. As the database grows, it can become a valuable tool in understanding brain disorders with respect to patient performance with real world activities.

Analysis by Skill Classification

Most cognitive skills can be classified as foundational, intermediate, or complex, with a few cognitive skills that apply at all levels. In an example, an assessment module can provide patient neurofunction assessment information including providing performance on cognitive skills grouped and displayed in a chart, e.g., using a neurological assessment tool, that illustrates the strengths and challenges within each cognitive skill classification, for example, such as illustrated in FIG. 4.

For each activity score of a single patient, the current performance will have a percent change from a baseline, where a baseline is any prior test, not necessarily just the prior test. The percent change can determine a strength or a challenge compared a previous performance. The patients activity score can be compared to a healthy population score to determine whether the patient has a strength or a challenge in that activity. Activity scores are generally classified into foundational, intermediate, or complex activities. In an example, as more patient data is stored in the computer assessment system, the weighting or regression analysis can be adjusted to determine an optimum formula for assessing mild to moderate brain disorders.

Analysis for Strengths and Challenges

In an example, the assessment module can be configured to provide patient neurofunction information to, e.g., to a user, such as by using a display on the neurological assessment tool. In general, it is dependent on the professional discipline on whether the change between baseline and the current comparison would be viewed as clinically significant to warrant further assessment for diagnosis or effectiveness of intervention. Within our assessment, at times, no change in results, a reduction in results, or an improvement in results would be desired clinically. Importantly, it can be how the results present combined that is clinically significant and useful. As such, the concept of clinical significance is not used in this assessment in its traditional form. Instead, the assessment module can determine patient strengths and challenges to assist clinicians in clinical reasoning and recommendations.

However, it is important to note that it is strongly recommended that the baseline and comparison method as described above is considered by the qualified health professional first. Results from this data allow a person to be directly compared to their own previous performance and any discrepancies can be reviewed for cause/diagnosis and amendments to intervention plan. Strengths and challenges in one's own neurofunction can be identified when comparing a person's own previous healthy baseline assessment to their current assessment performance. A strength remains when they perform at or above their own previous performance and a challenge is identified when they perform below their previous performance, after consideration to reliable change.

The comparison of a functional group that is matched for age range, education level, whether English is a second language and typing ability (on applicable questions) to a person's individual performance is intended to provide guidance to a healthy range of function and to better understand when a person functions above this range (strength) or below this range (challenge) compared to others. This analysis becomes particularly significant as a starting point for a person who may not have had a healthy baseline assessment completed. The analysis is completed using z-scores to determine if the score falls in 1.96 z-scores of the population, where $z=(x-mu/s)$, where mu is the population mean by age, education, second language, s is standard deviation. It is important to note that because we constantly add to our database, we are able to refresh the normative data as desired. In future, we will also compare a person who has had experienced a brain disorder to a like distribution.

Reliable Change (RC) is whether people have changed sufficiently that the change is unlikely to be due to simple measurement unreliability. It is determined by seeing if the difference between the comparison and baseline scores is more than a certain level. That level is a function of the initial standard deviation of the measure and its reliability.

The formula for the standard error of change is:

$$SD1*sqrt(2)*sqrt(1-rel), \qquad \text{Eq. 1}$$

where SD1 is the initial standard deviation, sqrt indicates the square root, rel indicates the reliability, preferably determined using the Cronenbach coefficient.

The formula for criterion level, based on chance that would happen less than 5% of the time by unreliability of measurement alone, is:

$$1.96*SD1*sqrt(2)*sqrt(1-rel). \qquad \text{Eq. 2}$$

The effect of statistical mitigators as identified in the above chart are used in data analysis. The Reliable Change from performance data is also compared to indicators of functional participation and satisfaction as obtained in the Questionnaire and Collateral-Report phases of the assessment.

In an example, consenting patients can choose to have their medical data mirrored to a Living Brain Bank, (after removing their identifying personal and health information), so that data for validation of the population can accrue without specific recruitment and be constantly available to qualified researchers for further study and validations.

Figure 2:
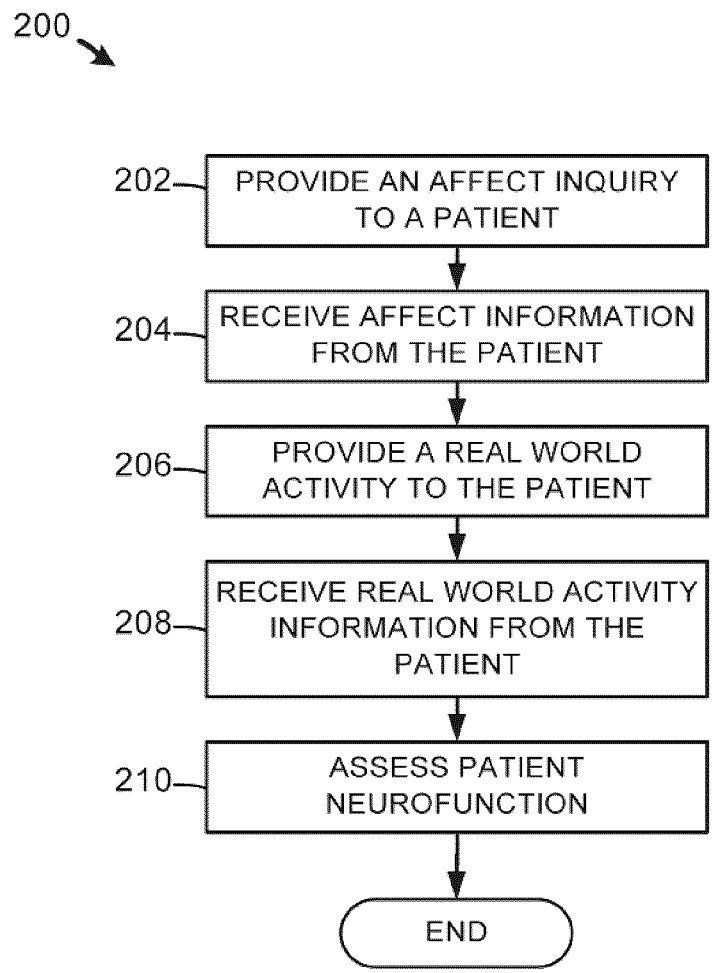
FIG. 2 illustrates generally an example computerized assessment method configured to assess patient neurofunction.

FIG. 2 illustrates generally an example computerized assessment method 200 configured to assess patient neurofunction. At 202, an affect inquiry can be provided to a patient, for example, using a neurological assessment tool. Various examples of affect inquiries are illustrated above in Table 3. At 204, affect information can be received from the patient in response to the provided affect inquiry.

At 206, a real world activity can be provided to the patient, for example, using the neurological assessment tool. Various examples of real world activities are illustrated above in Table 2. In an example, the specific real world activity or order or number of real world activities provided to the patient can depend at least in part on the affect information received from the patient. At 208, real world activity information can be received from the patient in response to the provided real world activity.

At 210, patient neurofunction can be assessed using the affect information and the real world activity information received from the patient. In various examples, patient neurofunction can be provided as identified strengths and challenges in real world functions, such as illustrated in FIGS. 3 and 4.

FIGS. 3 and 4 illustrate generally example neurofunction assessment information 300, 400. In other examples, other graphs or tables can be used to provide neurofunction assessment information to the patient, clinician, caregiver, or one or more other user.

FIG. 3 illustrates generally example patient neurofunction assessment information 400, including a graph of scored real world functions for a patient. In FIG. 3, each spoke illustrates a different cognitive skill. In an example, the cognitive skills can be expressed as real world functions. The score of each real world function can start at the center of the graph and increase as it nears the perimeter, with high scores extending farther from the center. In another example, the opposite can be true, where the scores increasing in value towards the center. Changes in strengths or challenges in specific functions can be illustrated with colors, for example, green illustrating an improvement over a past assessment or with respect to one or more other baseline, population or otherwise, and red illustrating the opposite. In other examples, other indicators different than colors can be used to illustrate changes or emphasis, such as arrows, text, etc.

FIG. 4 illustrates generally example neurofunction assessment information 400 including patient strengths and challenges in different categories of real world functions, including foundational skills, intermediate skills, and complex skills. In other examples, one or more other categories can be used, such as a universal category that transcends the foundational, intermediate, and complex categories. Examples of universal skills include comprehension, communication, information processing speed, endurance, etc.

Figure 5:
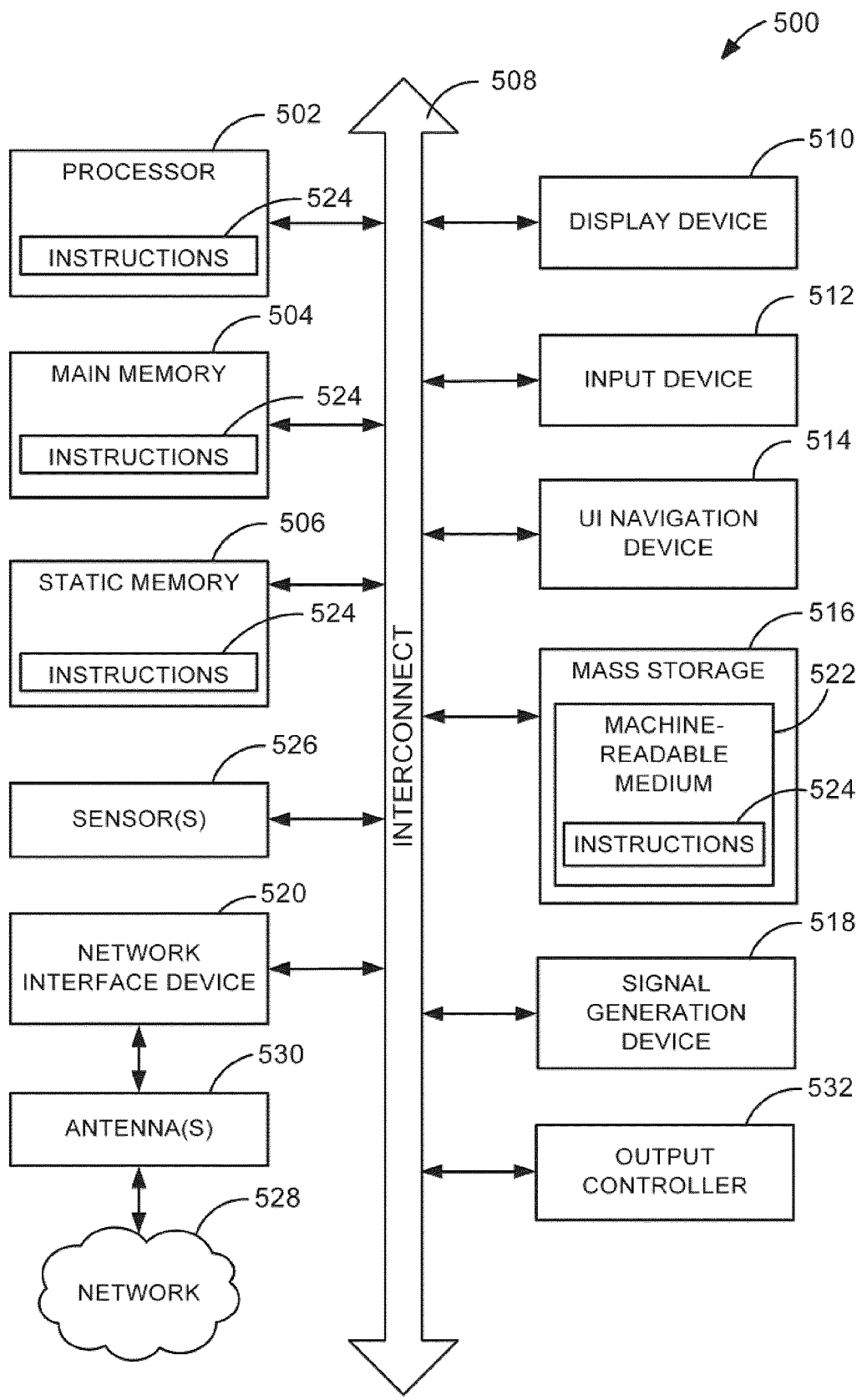
FIG. 5 illustrates generally an example computer system.

FIG. 5 illustrates generally an example computer system 500, within which a set or sequence of instructions may be executed to cause the machine to perform any one of the methodologies discussed herein, according to an example embodiment. Computer system machine 500 may be embodied by the electronic processing systems implemented by the servers 104 and database 106, the neurological assessment tool 102, or any other electronic processing or computing platform described or referred to herein.

Example computer system 500 includes at least one processor 502 (e.g., a central processing unit (CPU), a graphics processing unit (GPU) or both, processor cores, compute nodes, etc.), a main memory 504 and a static memory 506, which communicate with each other via an interconnect 508 (e.g., a link, a bus, etc.). The computer system 500 may further include a video display unit 510, an alphanumeric input device 512 (e.g., a keyboard), and a user interface (UI) navigation device 514 (e.g., a mouse). In one embodiment, the video display unit 510, input device 512 and UI navigation device 514 are incorporated into a touch-screen interface and touchscreen display. The computer system 500 may additionally include a storage device 516 (e.g., a drive unit), a signal generation device 518 (e.g., a speaker), an output controller 532, a network interface device 520 (which may include or operably communicate with one or more antennas 530, transceivers, or other wireless communications hardware), and one or more sensors 526, such as a global positioning system (GPS) sensor, compass, accelerometer, location sensor, or other sensor.

The storage device 516 includes a machine-readable medium 522 on which is stored one or more sets of data structures and instructions 524 (e.g., software) embodying or utilized by any one or more of the methodologies or functions described herein. The instructions 524 may also reside, completely or at least partially, within the main memory 504, static memory 506, and/or within the processor 502 during execution thereof by the computer system 500, with the main memory 504, static memory 506, and the processor 502 also constituting machine-readable media.

While the machine-readable medium 522 is illustrated in an example embodiment to be a single medium, the term "machine-readable medium" may include a single medium or multiple media (e.g., a centralized or distributed database, and/or associated caches and servers) that store the one or more instructions 524. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 524 may further be transmitted or received over a communications network 528 using a transmission medium via the network interface device 520 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 2G/3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Certain embodiments are described herein as including logic or a number of modules, components or mechanisms. A module, logic, component or mechanism (herein after collectively referred to as a "module") may be a tangible unit capable of performing certain operations and is configured or arranged in a certain manner. In example embodiments, one or more computer systems (e.g., a standalone, client or server computer system) or one or more components of a computer system (e.g., a processor or a group of processors) may be configured by software (e.g., an application or application portion) as a "module" that operates to perform certain operations as described herein.

In various embodiments, a "module" may be implemented mechanically or electronically. For example, a module may comprise dedicated circuitry or logic that is permanently configured (e.g., within a special-purpose processor) to perform certain operations. A module may also comprise programmable logic or circuitry (e.g., as encompassed within a general-purpose processor or other programmable processor) that is temporarily configured by software to perform certain operations. It will be appreciated that the decision to implement a module mechanically, in the dedicated and permanently configured circuitry, or in temporarily configured circuitry (e.g., configured by software) may be driven by cost and time considerations.

Accordingly, the term "module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which modules or components are temporarily configured (e.g., programmed), each of the modules or components need not be configured or instantiated at any one instance in time. For example, where the modules or components comprise a general-purpose processor configured using software, the general-purpose processor may be configured as respective different modules at different times. Software may accordingly configure the processor to constitute a particular module at one instance of time and to constitute a different module at a different instance of time.

Modules can provide information to, and receive information from, other modules. Accordingly, the described modules may be regarded as being communicatively coupled. Where multiple of such modules exist contemporaneously, communications may be achieved through signal transmission (e.g., over appropriate circuits and buses) that connect the modules. In embodiments in which multiple modules are configured or instantiated at different times, communications between such modules may be achieved, for example, through the storage and retrieval of information in memory structures to which the multiple modules have access. For example, a one module may perform an operation, and store the output of that operation in a memory device to which it is communicatively coupled. A further module may then, at a later time, access the memory device to retrieve and process the stored output. Modules may also initiate communications with input or output devices, and can operate on a resource (e.g., a collection of information).

Example Skill Performance

If a strength is identified, the skill associated with that strength can be color coded, for example, in green, if within similar healthy/selected impaired population. In contrast, if a challenge is identified, and said challenge is below the baseline, the challenge can be color coded with respect to the amount below the baseline. For example, if the challenge is between 1 and 2 standard deviations below a baseline, the challenge can be coded in a first color (e.g., yellow), and if the challenge is greater than 2 standard deviations below the baseline, the challenge can be coded in a second color (e.g., orange). Tables 8, below, illustrates an example skill performance.

TABLE 8

| Attention - Selective - to Visual Distraction | Results Feb. 14-12 | Results Jan. 22-13 | Real Life Applications |
|---|---|---|---|
| The ability to pay close attention to one aspect of information when presently visually despite other visual information competing for attention. | Find the Differences between two pictures: Easier: 6/6 differences Time to complete: X seconds More Difficult: 5/6 differences Time to complete: 20 seconds | Find the Differences between two pictures: Easier: 4/6 differences Time to complete: X seconds More Difficult: 2/6 differences Time to complete: 45 seconds | Reading magazines/ diagrams School work Work Paying bills |
| | Percent change b/w Date 1 and Date 2: 45% Decrease | | |

ADDITIONAL NOTES AND EXAMPLES

In Example 1, a computerized assessment system includes a neurological assessment tool configured to receive affect information from a patient in response to a provided affect inquiry and to receive real world activity information from the patient in response to a provided real world activity and an assessment module configured to provide patient neurofunction assessment information using the affect information and the real world activity information.

In Example 2, the provided real world activity of Example 1 optionally depends at least in part on the affect information received from the patient in response to the provided affect inquiry.

In Example 3, the provided affect inquiry of any one or more of Examples 1-2 optionally includes a first affect inquiry, wherein the provided real world activity of any one or more of Examples 1-2 optionally includes a first real world activity, and wherein the first affect inquiry is provided to the patient prior to the first real world activity.

In Example 4, the affect inquiry of any one or more of Examples 1-3 optionally includes a second affect inquiry provided to the patient after the real world activity.

In Example 5, the first real world activity of any one or more of Examples 1-4 optionally depends at least in part on the affect information received from the patient in response to the provided first affect inquiry.

In Example 6, the assessment module of any one or more of Examples 1-5 is optionally configured to identify the strengths and challenges in patient neurofunction using the affect information and the real world activity information and the patient neurofunction assessment information of any one or more of Examples 1-5 optionally includes patient strengths and challenges in real world function.

In Example 7, the strengths and challenges in real world function of any one or more of Examples 1-6 optionally includes at least one of: judgment for safety; foresight for safety; comprehension of humor; comprehension of inference; or event planning.

In Example 8, any one or more of Examples 1-7 optionally includes a collateral assessment module configured to receive collateral input from a third party separate from the patient in response to a collateral inquiry, wherein the assessment module of any one or more of Examples 1-7 is optionally configured to provide patient neurofunction assessment information using the affect information, the real world activity information, and the collateral input.

In Example 9, the neurological assessment tool of any one or more of Examples 1-8 optionally includes a web-enabled, portable, touch-screen tablet computer, and wherein the neurological assessment tool is configured to receive affect information and real world activity information from the patient using an input of the web-enabled, portable, touch-screen tablet computer.

In Example 10, the assessment module of any one or more of Examples 1-9 is optionally configured to receive and store affect information and real world activity information received from a plurality of patients, and to optionally provide the patient neurofunction assessment information using the affect information and the real world activity information received from the patient with respect to corresponding affect information and real world activity information received from the plurality of patients.

In Example 11, the affect information from the patient in any one or more of Examples 1-10 optionally includes at least one of: patient fatigue information; patient sleep information; patient anxiety information; patient mood information; or patient pain information.

In Example 12, a computerized assessment method includes receiving affect information from a patient, using a neurological assessment tool, in response to a provided affect inquiry, receiving real world activity information from the patient, using the neurological assessment tool, in response to a provided real world activity, and assessing, using an assessment module, patient neurofunction using the affect information and the real world activity information.

In Example 13, the method of Example 12 optionally includes providing an affect inquiry to the patient and providing a real world activity to the patient that depends at least in part on the received affect information in response to the provided affect inquiry.

In Example 14, any one or more of Examples 1-13 optionally include providing a first affect inquiry to the patient and providing a first real world activity to the patient, wherein the providing the first affect inquiry includes providing the first affect inquiry to the patient prior to providing the first real world activity to the patient.

In Example 15, any one or more of Examples 1-14 optionally include providing a second affect inquiry to the patient after providing the first real world activity to the patient.

In Example 16, the first real world activity of any one or more of Examples 1-15 optionally depends at least in part on affect information received from the patient in response to the provided first affect inquiry.

In Example 17, the assessing patient neurofunction of any one or more of Examples 1-16 optionally includes identifying patient strengths and challenges in real world function using the affect information and the real world activity information.

In Example 18, the strengths and challenges in real world function of any one or more of Examples 1-17 optionally includes at least one of: judgment for safety; foresight for safety; comprehension of humor; comprehension of inference; or event planning.

In Example 19, any one or more of Examples 1-18 optionally includes receiving collateral input from a third party separate from the patient, using a collateral assessment module, in response to a provided collateral inquiry, wherein the assessing patient neurofunction of any one or more of Examples 1-18 optionally includes using the affect information, the real world activity information, and the collateral input.

In Example 20, the receiving affect information and real world activity information from the patient in any one or more of Examples 1-19 optionally includes using an input of a web-enabled, portable, touch-screen tablet computer.

In Example 21, any one or more of Examples 1-20 optionally includes receiving and storing, using the assessment module, affect information and real world activity information from a plurality of patients, wherein the assessing patient neurofunction of any one or more of Examples 1-20 optionally includes using the affect information and the real world activity information received from the patient with respect to corresponding affect information and real world activity information received from the plurality of patients.

In Example 22, the receiving affect information from the patient of any one or more of Examples 1-21 optionally includes receiving at least one of: patient fatigue information; patient sleep information; patient anxiety information; patient mood information; or patient pain information.

In Example 23, a system or apparatus can include, or can optionally be combined with any portion or combination of any portions of any one or more of Examples 1-22 to include, means for performing any one or more of the functions of Examples 1-20, or a non-transitory machine-readable storage medium having instructions stored thereon that, when executed by a machine, cause the machine to perform any one or more of the methods or functions of Examples 1-22.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A computerized neurological assessment system for patients with mild to moderate cognitive impairments, comprising:
   a neurological assessment tool comprising a user interface configured to:
      receive background information from a patient including a patient level of experience with the user interface in response to a questionnaire addressing information leading up to assessment;
      receive affect information from the patient in response to a provided affect inquiry addressing a current condition of the patient while undergoing assessment;
      provide, using a touch-screen input of the user interface, simulations of real world activities to the patient on the touch-screen input while undergoing assessment from different cognitive skill categories, the different cognitive skill categories comprising a first cognitive skill category having real world activities of a first complexity and a second cognitive skill category having real world activities of a second complexity more complex than the first complexity, at least one of the simulations of real world activities comprising fine motor instructions to the patient with respect to one or more objects simulated on the touch-screen input, wherein fine motor instructions comprise instructions to touch the touch-screen input in a specific manner, wherein the instructions to touch comprise instructions to at least one of pinch or slide the one or more objects simulated on the touch-screen input; and
      receive real world activity information from the patient using the touch-screen input of the user interface in response to the provided simulations of the real world activities from each of the different cognitive skill categories, the real world activity information including fine motor interaction with respect to the touch-screen input, to provide patient interaction feedback of the fine motor interaction comprising at least one of a visual highlight using the touch-screen input of the user interface or a sound feedback using the user interface, and to determine a composite real world activity score for the patient for each of the different cognitive skill categories using the received real world activity information;
   a collateral assessment module configured to receive collateral input from a third party separate from the patient about a condition of the patient undergoing assessment in response to a collateral inquiry; and
   an assessment module configured to match the patient to a functional group of patients using the background information of the patient and information from a plurality of patients stored in a database, and to determine patient neurofunction assessment scores for each of the different cognitive skill categories comprising:
      a change score using a relationship between the determined real world activity scores for the patient and baseline information; and
      a population score using a comparison of the affect information received from the patient and the determined real world activity scores for the patient to affect information and real world activity information from the functional group of patients stored in the database,
   wherein the instructions to touch comprise instructions to pinch a first object at a first location and move the first object to a second location, wherein to provide patient interaction feedback comprises to provide a sound feedback associated with the pinch using the user interface and a visual highlight when the first object is at the second location, and wherein to determine the composite real world activity score for the patient comprises to determine at least one of a first time of the pinch or a second time to move the first object to the second location.

2. The computerized neurological assessment system of claim 1, wherein the provided affect inquiry includes a first affect inquiry, wherein the provided simulation of the real world activity includes a simulation of a first real world activity, and wherein the first affect inquiry is provided to the patient prior to the simulation of the first real world activity.

3. The computerized neurological assessment system of claim 2, wherein the affect inquiry includes a second affect inquiry provided to the patient after the simulation of the first real world activity.

4. The computerized neurological assessment system of claim 2, wherein the simulation of the first real world activity depends at least in part on the affect information received from the patient in response to the provided first affect inquiry.

5. The computerized neurological assessment system of claim 1, wherein the assessment module is configured to identify the strengths and challenges in patient neurofunction using the affect information and the real world activity information by comparing the received affect information and the real world activity information to baseline information, wherein the patient neurofunction assessment information includes patient strengths and challenges in real world function, and wherein the strengths and challenges in real world function includes at least one of:
  judgment for safety;
  foresight for safety;
  comprehension of humor;
  comprehension of inference; or
  event planning.

6. The computerized neurological assessment system of claim 1, wherein the affect information from the patient includes at least one of:
  patient fatigue information at the time of assessment;
  patient sleep information the night prior to assessment;
  patient anxiety information at the time of assessment;
  patient mood information at the time of assessment; or
  patient pain information at the time of assessment.

7. The computerized neurological assessment system of claim 1, wherein at least one of the simulations of real world activities comprises an auditory presentation to the patient, and wherein the received real world activity information from the patient comprises a touch-screen input from the patient on the user interface in response to the provided auditory presentation to the patient.

8. The computerized neurological assessment system of claim 1, wherein at least one of the real world activities comprises a temporal awareness inquiry including a request for an estimate of time since starting the assessment, wherein to receive real world activity information from the patient comprises receiving an estimate of time, and wherein to determine the composite real world activity score comprises to determine a difference between the received estimate and the time since starting the assessment.

9. The computerized neurological assessment system of claim 1, wherein the instructions to touch comprise instructions to select one or more objects simulated on the touch-screen input at a first location, and then move the selected one or more objects to a second location on the touch-screen input.

10. The computerized neurological assessment system of claim 9, wherein the instructions to select the one or more objects includes instructions to touch or pinch the one or more objects, and the instructions to move the selected one or more objects to the second location include instructions to slide the selected one or more objects on the touch-screen input to the second location.

11. A computerized neurological assessment method for patients with mild to moderate cognitive impairments, comprising:

receiving, using a user interface of a neurological assessment tool, background information from a patient including a patient level of experience with the user interface in response to a questionnaire addressing information leading up to assessment;

receiving affect information from the patient, using the neurological assessment tool, in response to a provided affect inquiry addressing a current condition of the patient while undergoing assessment;

providing, using a touch-screen input of the user interface, simulations of real world activities to the patient on the touch-screen input from different cognitive skill categories, the different cognitive skill categories comprising a first cognitive skill category having real world activities of a first complexity and a second cognitive skill category having real world activities of a second complexity more complex than the first complexity, at least one of the simulations of real world activities comprising fine motor instructions to the patient with respect to one or more objects simulated on the touch-screen input, wherein fine motor instructions comprise instructions to touch the touch-screen input in a specific manner, wherein the instructions to touch comprise instructions to at least one of pinch or slide the one or more objects simulated on the touch-screen input;

receiving real world activity information from the patient, using the touch-screen input of the user interface, in response to the provided simulations of the real world activities from each of the different cognitive skill categories, the real world activity information including fine motor interaction with respect to the touch-screen input;

providing patient interaction feedback of the fine motor interaction comprising at least one of a visual highlight using the touch-screen input of the user interface or a sound feedback using the user interface;

determining a composite real world activity score for the patient for each of the different cognitive skill categories using the received real world activity information;

receiving collateral input from a third party separate from the patient about a condition of the patient undergoing assessment in response to a collateral inquiry using a collateral assessment module;

matching the patient to a functional group of patients using the background information of the patient and information from a plurality of patients stored in a database using an assessment module; and determining, using the assessment module, patient neurofunction assessment scores for each of the different cognitive skill categories, comprising:

determining a change score using a relationship between the determined real world activity scores for the patient and baseline information; and determining a population score using a comparison of the received affect information received from the patient and the determined real world activity scores for the patient to affect information and real world activity information from the functional group of patients stored in the database, wherein the instructions to touch comprise instructions to pinch a first object at a first location and move the first object to a second location, wherein the providing patient interaction feedback comprises providing a sound feedback associated with the pinch using the user interface and a visual highlight when the first object is at the second location, and wherein the determining the composite real world activity score for the patient comprises determining at least one of a first time of the pinch or a second time to move the first object to the second location.

12. The computerized neurological assessment method of claim 11, including:
providing a first affect inquiry to the patient,
wherein the providing the first affect inquiry includes providing the first affect inquiry to the patient prior to determining the simulation of the real world activity to provide to the patient.

13. The computerized neurological assessment method of claim 12, including:
providing a second affect inquiry to the patient after providing the simulation of the real world activity to the patient.

14. The computerized neurological assessment method of claim 11, wherein the assessing patient neurofunction includes identifying patient strengths and challenges in real world function using the affect information and the real world activity information by comparing the received affect information and the real world activity information to baseline information, and
wherein the strengths and challenges in real world function includes at least one of:
judgment for safety;
foresight for safety;
comprehension of humor;
comprehension of inference; or
event planning.

15. The computerized neurological assessment system of method 11, including:
receiving and storing, using the assessment module, affect information and real world activity information from the plurality of patients in the database.

16. The computerized neurological assessment method of claim 11, wherein the receiving affect information from the patient includes receiving at least one of:
patient fatigue information at the time of assessment;
patient sleep information the night prior to assessment;
patient anxiety information at the time of assessment;
patient mood information at the time of assessment; or
patient pain information at the time of assessment.

17. A non-transitory machine-readable storage medium having instructions stored thereon that, when executed by a machine, cause the machine to perform operations comprising:
receiving, using a user interface, background information from a patient including a patient level of experience with the user interface in response to a questionnaire addressing information leading up to assessment;

receiving affect information from the patient in response to a provided affect inquiry addressing a current condition of the patient while undergoing assessment;

providing, using a touch-screen input of the user interface, simulations of real world activities to the patient on the touch-screen input from different cognitive skill categories, the different cognitive skill categories comprising a first cognitive skill category having real world activities of a first complexity and a second cognitive skill category having real world activities of a second complexity more complex than the first complexity, at least one of the simulations of real world activities comprising fine motor instructions to the patient with respect to one or more objects simulated on the touch-screen input, wherein fine motor instructions comprise instructions to touch the touch-screen input in a specific manner, wherein the instructions to touch comprise instructions to at least one of pinch or slide the one or more objects simulated on the touch-screen input;

receiving real world activity information from the patient, using the touch-screen input of the user interface, in response to the provided simulations of the real world activities from each of the different cognitive skill categories, the real world activity information including fine motor interaction with respect to the touch-screen input;

providing patient interaction feedback of the fine motor interaction comprising at least one of a visual highlight using the touch-screen input of the user interface or a sound feedback using the user interface;

determining a composite real world activity score for the patient for each of the different cognitive skill categories using the received real world activity information;

receiving collateral input from a third party separate from the patient about a condition of the patient undergoing assessment in response to a collateral inquiry using a collateral assessment module;

matching the patient to a functional group of patients using the background information of the patient and information from a plurality of patients stored in a database using an assessment module; and determining, using the assessment module, patient neurofunction assessment scores for each of the different cognitive skill categories, comprising:
determining a change score using a relationship between the determined real world activity scores for the patient and baseline information; and determining a population score using a comparison of the received affect information received from the patient and the determined real world activity scores for the patient to affect information and real world activity information from the functional group of patients stored in the database, wherein the instructions to touch comprise instructions to pinch a first object at a first location and move the first object to a second location, wherein the providing patient interaction feedback comprises providing a sound feedback associated with the pinch using the user interface and a visual highlight when the first object is at the second location, and wherein the determining the composite real world activity score for the patient comprises determining at least one of a first time of the pinch or a second time to move the first object to the second location.

18. The non-transitory machine-readable storage medium of claim 17, wherein the operations further comprise:
providing a first affect inquiry to the patient, wherein the providing the first affect inquiry includes providing the first affect inquiry to the patient prior to determining the simulation of the real world activity to provide to the patient; and
providing a second affect inquiry to the patient after providing the simulation of the real world activity to the patient.

19. The non-transitory machine-readable storage medium of claim 17, wherein the assessing patient neurofunction includes identifying patient strengths and challenges in real world function using the affect information and the real world activity information by comparing the received affect information and the real world activity information to baseline information.

20. A computerized neurological assessment system for patients with mild to moderate cognitive impairments, comprising:
a neurological assessment tool comprising a user interface configured to:
receive background information from a patient including a patient level of experience with the user interface in response to a questionnaire addressing information leading up to assessment;
receive affect information from the patient in response to a provided affect inquiry addressing a current condition of the patient while undergoing assessment;
provide, using a touch-screen input of the user interface, simulations of real world activities to the patient on the touch-screen input while undergoing assessment from different cognitive skill categories, the different cognitive skill categories comprising a first cognitive skill category having real world activities of a first complexity and a second cognitive skill category having real world activities of a second complexity more complex than the first complexity, at least one of the simulations of real world activities comprising fine motor instructions to the patient with respect to one or more objects simulated on the touch-screen input, wherein fine motor instructions comprise instructions to touch the touch-screen input in a specific manner, wherein the instructions to touch comprise instructions to at least one of pinch or slide the one or more objects simulated on the touch-screen input; and
receive real world activity information from the patient using the touch-screen input of the user interface in response to the provided simulations of the real world activities from each of the different cognitive skill categories, the real world activity information including fine motor interaction with respect to the touch-screen input, to provide patient interaction feedback of the fine motor interaction comprising at least one of a visual highlight using the touch-screen input of the user interface or a sound feedback using the user interface, and to determine a composite real world activity score for the patient for each of the different cognitive skill categories using the received real world activity information;
a collateral assessment module configured to receive collateral input from a third party separate from the patient about a condition of the patient undergoing assessment in response to a collateral inquiry; and
an assessment module configured to match the patient to a functional group of patients using the background information of the patient and information from a plurality of patients stored in a database, and to determine patient neurofunction assessment scores for each of the different cognitive skill categories comprising:
a change score using a relationship between the determined real world activity scores for the patient and baseline information; and
a population score using a comparison of the affect information received from the patient and the determined real world activity scores for the patient to affect information and real world activity information from the functional group of patients stored in the database,
wherein the instructions to touch comprise instructions to touch the touch-screen input in a specific manner, including a first touch with a left hand and a second touch with a right hand, and
wherein to determine the composite real world activity score for the patient comprises to determine a time associated with the first touch and a time associated with the second touch.

21. A computerized neurological assessment method for patients with mild to moderate cognitive impairments, comprising:
receiving, using a user interface of a neurological assessment tool, background information from a patient including a patient level of experience with the user interface in response to a questionnaire addressing information leading up to assessment;
receiving affect information from the patient, using the neurological assessment tool, in response to a provided affect inquiry addressing a current condition of the patient while undergoing assessment;
providing, using a touch-screen input of the user interface, simulations of real world activities to the patient on the touch-screen input from different cognitive skill categories, the different cognitive skill categories comprising a first cognitive skill category having real world activities of a first complexity and a second cognitive skill category having real world activities of a second complexity more complex than the first complexity, at least one of the simulations of real world activities comprising fine motor instructions to the patient with respect to one or more objects simulated on the touch-screen input, wherein fine motor instructions comprise instructions to touch the touch-screen input in a specific manner, wherein the instructions to touch comprise instructions to at least one of pinch or slide the one or more objects simulated on the touch-screen input;
receiving real world activity information from the patient, using the touch-screen input of the user interface, in response to the provided simulations of the real world activities from each of the different cognitive skill categories, the real world activity information including fine motor interaction with respect to the touch-screen input;
providing patient interaction feedback of the fine motor interaction comprising at least one of a visual highlight using the touch-screen input of the user interface or a sound feedback using the user interface;
determining a composite real world activity score for the patient for each of the different cognitive skill categories using the received real world activity information;
receiving collateral input from a third party separate from the patient about a condition of the patient undergoing assessment in response to a collateral inquiry using a collateral assessment module;

matching the patient to a functional group of patients using the background information of the patient and information from a plurality of patients stored in a database using an assessment module; and determining, using the assessment module, patient neurofunction assessment scores for each of the different cognitive skill categories, comprising:
  determining a change score using a relationship between the determined real world activity scores for the patient and baseline information; and
  determining a population score using a comparison of the received affect information received from the patient and the determined real world activity scores for the patient to affect information and real world activity information from the functional group of patients stored in the database, wherein the instructions to touch comprise instructions to touch the touch-screen input in a specific manner, including a first touch with a left hand and a second touch with a right hand, and wherein to determine the composite real world activity score for the patient comprises to determine a time associated with the first touch and a time associated with the second touch.

22. A non-transitory machine-readable storage medium having instructions stored thereon that, when executed by a machine, cause the machine to perform operations comprising:

receiving, using a user interface, background information from a patient including a patient level of experience with the user interface in response to a questionnaire addressing information leading up to assessment;

receiving affect information from the patient in response to a provided affect inquiry addressing a current condition of the patient while undergoing assessment;

providing, using a touch-screen input of the user interface, simulations of real world activities to the patient on the touch-screen input from different cognitive skill categories, the different cognitive skill categories comprising a first cognitive skill category having real world activities of a first complexity and a second cognitive skill category having real world activities of a second complexity more complex than the first complexity, at least one of the simulations of real world activities comprising fine motor instructions to the patient with respect to one or more objects simulated on the touch-screen input, wherein fine motor instructions comprise instructions to touch the touch-screen input in a specific manner, wherein the instructions to touch comprise instructions to at least one of pinch or slide the one or more objects simulated on the touch-screen input;

receiving real world activity information from the patient, using the touch-screen input of the user interface, in response to the provided simulations of the real world activities from each of the different cognitive skill categories, the real world activity information including fine motor interaction with respect to the touch-screen input;

providing patient interaction feedback of the fine motor interaction comprising at least one of a visual highlight using the touch-screen input of the user interface or a sound feedback using the user interface;

determining a composite real world activity score for the patient for each of the different cognitive skill categories using the received real world activity information;

receiving collateral input from a third party separate from the patient about a condition of the patient undergoing assessment in response to a collateral inquiry using a collateral assessment module;

matching the patient to a functional group of patients using the background information of the patient and information from a plurality of patients stored in a database using an assessment module; and determining, using the assessment module, patient neurofunction assessment scores for each of the different cognitive skill categories, comprising:
  determining a change score using a relationship between the determined real world activity scores for the patient and baseline information; and
  determining a population score using a comparison of the received affect information received from the patient and the determined real world activity scores for the patient to affect information and real world activity information from the functional group of patients stored in the database, wherein the instructions to touch comprise instructions to touch the touch-screen input in a specific manner, including a first touch with a left hand and a second touch with a right hand, and wherein to determine the composite real world activity score for the patient comprises to determine a time associated with the first touch and a time associated with the second touch.

23. A computerized neurological assessment system for patients with mild to moderate cognitive impairments, comprising:

a neurological assessment tool comprising a user interface configured to:
  receive background information from a patient including a patient level of experience with the user interface in response to a questionnaire addressing information leading up to assessment;
  receive affect information from the patient in response to a provided affect inquiry addressing a current condition of the patient while undergoing assessment;
  provide, using a touch-screen input of the user interface, simulations of real world activities to the patient on the touch-screen input while undergoing assessment from different cognitive skill categories, the different cognitive skill categories comprising a first cognitive skill category having real world activities of a first complexity and a second cognitive skill category having real world activities of a second complexity more complex than the first complexity, at least one of the simulations of real world activities comprising fine motor instructions to the patient with respect to one or more objects simulated on the touch-screen input, wherein fine motor instructions comprise instructions to touch the touch-screen input in a specific manner, wherein the instructions to touch comprise instructions to at least one of pinch or slide the one or more objects simulated on the touch-screen input; and
  receive real world activity information from the patient using the touch-screen input of the user interface in response to the provided simulations of the real world activities from each of the different cognitive skill categories, the real world activity information including fine motor interaction with respect to the touch-screen input, to provide patient interaction feedback of the fine motor interaction comprising at least one of a visual highlight using the touch-screen input of the user interface or a sound feedback using the user interface, and to determine a composite real world activity score for the patient for each of the different cognitive skill categories using the received real world activity information;
a collateral assessment module configured to receive collateral input from a third party separate from the patient about a condition of the patient undergoing assessment in response to a collateral inquiry; and
an assessment module configured to match the patient to a functional group of patients using the background information of the patient and information from a plurality of patients stored in a database, and to determine patient neurofunction assessment scores for each of the different cognitive skill categories comprising:
a change score using a relationship between the determined real world activity scores for the patient and baseline information; and
a population score using a comparison of the affect information received from the patient and the determined real world activity scores for the patient to affect information and real world activity information from the functional group of patients stored in the database,
wherein the instructions to touch comprise instructions to alternatingly pinch objects with left and right hands and move the objects from a first location to a second location,
wherein to provide patient interaction feedback comprises to provide a sound feedback associated with each pinch using the user interface and a visual highlight when the objects are at the second location, and
wherein to determine the composite real world activity score for the patient comprises to determine, for each of the left and right hands, at least one of a time associated with the pinching the objects or a time associated with moving to the objects to the second location.

24. A computerized neurological assessment method for patients with mild to moderate cognitive impairments, comprising:
receiving, using a user interface of a neurological assessment tool, background information from a patient including a patient level of experience with the user interface in response to a questionnaire addressing information leading up to assessment;
receiving affect information from the patient, using the neurological assessment tool, in response to a provided affect inquiry addressing a current condition of the patient while undergoing assessment;
providing, using a touch-screen input of the user interface, simulations of real world activities to the patient on the touch-screen input from different cognitive skill categories, the different cognitive skill categories comprising a first cognitive skill category having real world activities of a first complexity and a second cognitive skill category having real world activities of a second complexity more complex than the first complexity, at least one of the simulations of real world activities comprising fine motor instructions to the patient with respect to one or more objects simulated on the touch-screen input, wherein fine motor instructions comprise instructions to touch the touch-screen input in a specific manner, wherein the instructions to touch comprise instructions to at least one of pinch or slide the one or more objects simulated on the touch-screen input;

receiving real world activity information from the patient, using the touch-screen input of the user interface, in response to the provided simulations of the real world activities from each of the different cognitive skill categories, the real world activity information including fine motor interaction with respect to the touch-screen input;
providing patient interaction feedback of the fine motor interaction comprising at least one of a visual highlight using the touch-screen input of the user interface or a sound feedback using the user interface;
determining a composite real world activity score for the patient for each of the different cognitive skill categories using the received real world activity information;
receiving collateral input from a third party separate from the patient about a condition of the patient undergoing assessment in response to a collateral inquiry using a collateral assessment module;
matching the patient to a functional group of patients using the background information of the patient and information from a plurality of patients stored in a database using an assessment module; and
determining, using the assessment module, patient neurofunction assessment scores for each of the different cognitive skill categories, comprising:
determining a change score using a relationship between the determined real world activity scores for the patient and baseline information; and
determining a population score using a comparison of the received affect information received from the patient and the determined real world activity scores for the patient to affect information and real world activity information from the functional group of patients stored in the database,
wherein the instructions to touch comprise instructions to alternatingly pinch objects with left and right hands and move the objects from a first location to a second location,
wherein to provide patient interaction feedback comprises to provide a sound feedback associated with each pinch using the user interface and a visual highlight when the objects are at the second location, and
wherein to determine the composite real world activity score for the patient comprises to determine, for each of the left and right hands, at least one of a time associated with the pinching the objects or a time associated with moving to the objects to the second location.

25. A non-transitory machine-readable storage medium having instructions stored thereon that, when executed by a machine, cause the machine to perform operations comprising:
receiving, using a user interface, background information from a patient including a patient level of experience with the user interface in response to a questionnaire addressing information leading up to assessment;
receiving affect information from the patient in response to a provided affect inquiry addressing a current condition of the patient while undergoing assessment;
providing, using a touch-screen input of the user interface, simulations of real world activities to the patient on the touch-screen input from different cognitive skill categories, the different cognitive skill categories comprising a first cognitive skill category having real world activities of a first complexity and a second cognitive skill category having real world activities of a second complexity more complex than the first complexity, at least one of the simulations of real world activities comprising fine motor instructions to the patient with respect to one or more objects simulated on the touch-screen input, wherein fine motor instructions comprise instructions to touch the touch-screen input in a specific manner, wherein the instructions to touch comprise instructions to at least one of pinch or slide the one or more objects simulated on the touch-screen input;

receiving real world activity information from the patient, using the touch-screen input of the user interface, in response to the provided simulations of the real world activities from each of the different cognitive skill categories, the real world activity information including fine motor interaction with respect to the touch-screen input;

providing patient interaction feedback of the fine motor interaction comprising at least one of a visual highlight using the touch-screen input of the user interface or a sound feedback using the user interface;

determining a composite real world activity score for the patient for each of the different cognitive skill categories using the received real world activity information;

receiving collateral input from a third party separate from the patient about a condition of the patient undergoing assessment in response to a collateral inquiry using a collateral assessment module;

matching the patient to a functional group of patients using the background information of the patient and information from a plurality of patients stored in a database using an assessment module; and determining, using the assessment module, patient neurofunction assessment scores for each of the different cognitive skill categories, comprising:

determining a change score using a relationship between the determined real world activity scores for the patient and baseline information; and determining a population score using a comparison of the received affect information received from the patient and the determined real world activity scores for the patient to affect information and real world activity information from the functional group of patients stored in the database, wherein the instructions to touch comprise instructions to alternatingly pinch objects with left and right hands and move the objects from a first location to a second location, wherein to provide patient interaction feedback comprises to provide a sound feedback associated with each pinch using the user interface and a visual highlight when the objects are at the second location, and wherein to determine the composite real world activity score for the patient comprises to determine, for each of the left and right hands, at least one of a time associated with the pinching the objects or a time associated with moving to the objects to the second location.

\* \* \* \* \*